March 6, 1973 D. L. ARMSTRONG Plant Pat. 3,314
ROSE PLANT
Filed April 15, 1971
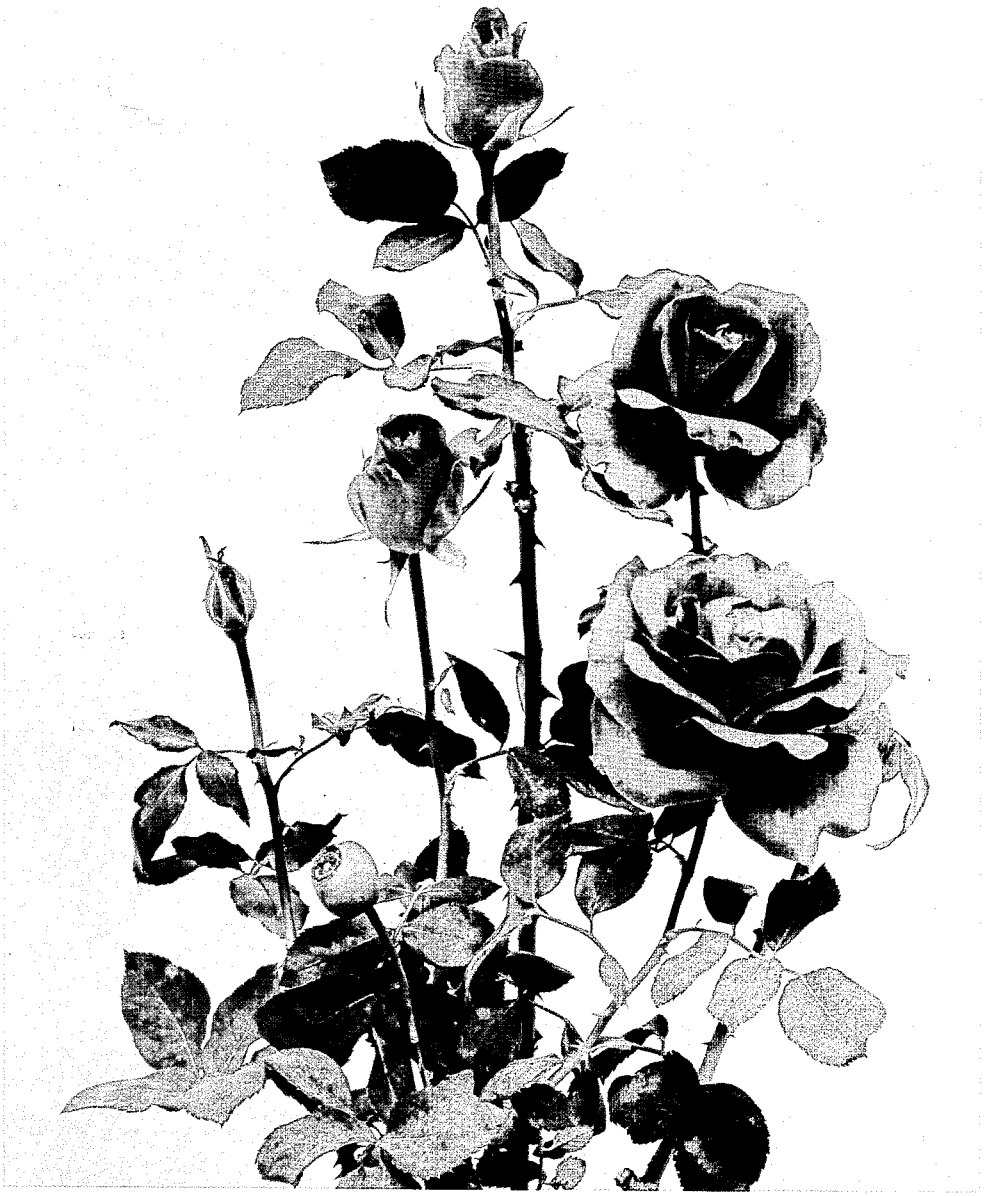

United States Patent Office

Plant Pat. 3,314
Patented Mar. 6, 1973

3,314
ROSE PLANT

David L. Armstrong, Upland, Calif., assignor to Armstrong Nurseries, Inc., Ontario, Calif.

Filed Apr. 15, 1971, Ser. No. 134,519
Int. Cl. A01h 5/00
U.S. Cl. Plt.—20 1 Claim

ABSTRACT OF THE DISCLOSURE

A new variety of rose of the hybrid tea class which bears very large blooms on strong, medium-length stems. The blooms are usually borne singly, but sometimes two or three appear on a stem in an irregular cluster. The flower, which is of double petalage, may span as much as 6 inches when fully open, and may contain as many as 50 petals. The plant blooms freely outdoors and nearly continuously during the growing season. The general color effect of the newly opened flower is strong purplish red. Its fragrance is a moderate to strong damask.

This invention relates to a new rose plant of the hybrid tea class. The plant is a seedling of the half-hardy, tall, bush type, cultivated for cut flowers and garden decoration. It was propagated by David L. Armstrong in Ontario, Calif., having as its seed parent "Manitou" (not patented) and, as its pollen parent, "Grand Slam" (Plant Patent 2,187). It holds its distinguishing characteristics through succeeding propagations by budding.

The flowers of this new variety are usually borne singly, on strong, medium-length stems, but sometimes two or three blooms are observed in an irregular cluster on a single stem. The plant blooms freely outdoors, and nearly continuously during the growing season. It has a moderate to strong damask fragrance.

Differences between this new variety of rose plant and its seed parent, Manitou, include the following:

Although both varieties may be described as upright-spreading, the growth habit of this new cultivar is substantially more spreading than of Manitou. Furthermore, although the leaves of Manitou are extremely large and quite glossy in surface appearance, the leaves of this new cultivar are semiglossy in appearance, and range from medium to large in size.

Whereas this new variety has flowers which might popularly be described as light red or deep pink, the flowers of Manitou may be described as a red blend, cerise to flame red on the inner surface and cerise to gold on the reverse, with gold predominating at the base. The flowers of this new cultivar have a moderate to strong fragrance, whereas the fragrance of the Manitou flowers is very strong.

The hips of this new variety are of medium to large size, whereas the hips of its seed parent, Manitou, are extremely large on attaining their ultimate size. Furthermore, the hips of this new cultivar are usually somewhat russeted at maturity, whereas the hips of Manitou rarely show any russeting, but often display varying degrees of red and yellow.

Differences between this new cultivar and its pollen parent, Grand Slam, include the following:

Whereas there are a limited number of stipitate glands and small prickles on the peduncles of Grand Slam, there is an almost complete absence of both on the peduncles of this new variety.

The flowers of this new variety may be popularly described as deep pink or light red, whereas the flowers of Grand Slam would be appropriately referred to as medium red—more specifically, cherry to rose-red.

The fragrance of the flowers of this new cultivar ranges from moderate to strong, whereas the flowers of the pollen parent, Grand Slam, have little or no fragrance.

The hips of Grand Slam are relatively small, for rose plants of the hybrid tea class, whereas the hips of this new cultivar are moderately large.

The accompanying drawing illustrates the plant in color and shows the flowering thereof from bud to full bloom.

Throughout this specification, color names beginning with a small letter signify that the name of that color, as used in common speech, is aptly descriptive. Color names beginning with a capital letter designate values based upon the Nickerson Color Fan, put out by Munsell Color Co.

*Bud*

The peduncle is average length, average caliper, and erect. It is usually smooth, and carries a few gland-tipped cilia. Its color is near Strong Yellow Green, 2.5GY 6/8, overlaid with near Light Olive, 7.5Y 5/5, in areas exposed to the sun.

Before the calyx breaks, the bud is of medium size, medium length, and ovoid in form.

As the calyx breaks, the color is near Dark Red, 5R 3/7. The inner surface of the sepals carries a fine, woolly tomentum.

The margins of alternate sepals are lined with fine, woolly tomentum; margins of others sometimes have a few small stipitate glands and small slender foliaceous appendages. These foliaceous appendages usually extend from one-quarter to one-half of the sepal length. The outside surface of the sepals is usually smooth.

As the first petal opens, it is from average to large in size, medium-length to long, and urn-shaped. Its color on the outside is between Strong Purplish Red, 7.5RP 4/11, and Strong Purplish Red, 10RP 4/12. On the inside, the color is between Strong Purplish Red, 7.5RP 4/11, and Deep Purplish Red, 10RP 3/10. The bud opens up well, and is not retarded or prevented from opening by cold, hot, wet, or dry weather.

*Bloom*

The size of the bloom when fully open is very large, being from five to six inches. The petalage is double, with from 45 to 50 petals arranged irregularly, and with from three to five petaloids. The bloom is high-centered at first, becoming cupped to high-centered at maturity.

At first, the petals are somewhat tightly cupped, with tips reflexed outward, becoming later at maturity loosely flat to cupped, with tips reflexed outward.

The petals are of medium thickness, with inside velvety and outside satiny. The outside petals are between round and broadly obovate, with apex flat, and usually with one to three notches. Both the intermediate and inside petals are broadly obovate, with apex rounded, and sometimes with one or two notches. The colors may be modified by being shaded and/or washed with other colors.

The paragraphs immediately following describe color values observed in a flower newly opened in the month of October. The plant had been grown outdoors, in Ontario, California.

The outer surface of the outside petal is between Strong Purplish Red, 7.5RP 4/11, and Strong Purplish Red, 10RP 4/12. The inner surface of the outside petal is near Strong Purplish Red, 10RP 4/12.

The outer surface of the intermediate petal is between Strong Purplsh Red, 7.5RP 5/12, and Strong Purplish Red, 10RP 4/12. The inner surface of the intermediate petal is near Strong Purplsh Red, 10RP 4/12.

The outer surface of the inner petal is between Strong Purplish Red, 7.5RP 4/11, and Strong Purplish Red, 10RP 4/12. The inner surface of the inner petal is between Moderate Red, 2.5R 4/10, and Deep Purplish Red, 10RP 3/10.

The paragraphs immediately following describe the color values observed in a bloom which had been open for three days, outdoors, in the month of October. The plant had been grown outdoors, in Ontario, California.

Both the outer surface and the inner surface of the outside petal was between Strong Purplish Red, 7.5RP 4/11, and Strong Purplish Red, 10RP 4/12.

The inside petal showed the same color characteristics as the outside petal.

The general color effect of the newly opened flower is near Strong Purplish Red, 10RP 4/12. After three days open, the color effect was between Strong Purplish Red, 7.5RP 5/12, and Strong Purplish Red, 10RP 4/12. The petals drop off cleanly, and are not particularly affected by cold, hot, wet, or dry weather.

The flower on the bush in the garden persists for four to five days in the month of October, in the locality named. Cut roses grown outdoors and kept at living-room temperatures will last for three or four days in the month of October.

*Reproductive organs*

Stamens: The stamens are average in number, arranged regularly about the pistils. A few are mixed with petaloids.

Filaments: The filaments are medium length, being about 6 to 12 mm. long, and near Moderate Orange Yellow, 7.5YR 8/8, in color. Most are with anthers.

Anthers: The anthers are medium size, all opening approximately at once. On both the upper and under side, the margins are near Strong Organe Yellow, 7.5YR 7/11, and central area is near Pale Orange Yellow, 7.5YR 9/4.

Pollen: The pollen is abundant, and near Moderate Orange Yellow, 10YR 8/10, in color.

Pistils: The pistils are approximately 60 in number, this being average.

Styles: The styles are uneven, short to average in length, thin in caliper, and bunched. The upper one-third of the style is near Strong Purplish Red, 10RP 4/12, the remainder being near Brilliant Greenish Yellow, 7.5Y 9/8.

Stigma: The stigma is near Light Orange, 5YR 8/7, in color.

Ovaries: Usually all of the ovaries are enclosed in the calyx.

Hips: The hips are globular in shape, with smooth, thick, fleshy, but russeted, walls. Their color is near Strong Yellow, 5Y 7/10.

Sepals: The sepals fall soon. They are medium-length to long, and may vary in shape, being straight, spear-shaped, curled, or recurved. Their color on the inside is near Pale Orange Yellow, 7.5YR 9/4, and on the outside near Brilliant Yellow, 5Y 9/9.

Seeds: Seeds are few in number, from twelve to twenty, and are of medium size.

*Foliage*

The compound leaves usually comprise from three to seven leaflets. They are abundant, medium to large in size, leathery, and semi-glossy. The leaflets are ovoid, with apex acute, base round, and margin simply serrate.

The mature foliage displays upon its upper surface a color which is between Grayish Olive Green, 5GY 3/2, and Moderate Olive Green, 5GY 4/3. The under surface is between Moderate Yellow Green, 5GY 5/6, and Moderate Yellow Green, 7.5GY 5/7.

The young foliage on its upper surface is between Moderate Olive, 7.5Y 4/3, and Moderate Olive, 10Y 4/3. On its under surface it is near Dark Greenish Yellow, 10Y 6/7, with the veins near Moderate Reddish Brown, 7.5R 3/6.

The rachis is of average size, being grooved, with a few to several stipitate glands on the edges on its upper side. On its under side it is smooth, except that sometimes a few small prickles appear.

The stipules are medium-length, narrow, and with short points turning out at an angle of less than 45°.

The plant displays an average resistance to mildew, as compared, under comparable conditions, with other varieties grown at Ontario, Calif.

*Growth*

The plant displays a free to vigorous upright-spreading and much branched habit of growth. Its canes are of medium to heavy caliper.

The main stems are near Light Olive, 10Y 5/5, in color. There are several large prickles, these being medium-length and hooked slightly downward, with short to medium-length, moderately broad bases. Their color is near Moderate Reddish Brown, 2.5YR 3/3. There are a few small prickles, and their color is the same as that of the large prickles. There are no hairs.

The branches are near Strong Yellow Green, 2.5GY 6/8, in color. There are several large prickles, these being moderately short and hooked slightly downward, with short, moderately broad bases. Their color is near Strong Brown, 5YR 4/5. There are a few small prickles, and their color is the same as that of the large prickles. There are no hairs.

New shoots are near Strong Yellow Green, 2.5GY 6/8, overlaid with near Moderate Reddish Brown, 2.5YR 3/3, in areas exposed to the sun. There are several medium-length large prickles, these being hooked slightly downward, with short, moderately broad bases. Their color is near Moderate Reddish Brown, 10R 3/4. There are a few small prickles, and their color is the same as that of the large prickles. There are no hairs.

I claim:

1. The new variety of rose plant substantially as herein shown and described, manifesting, in combination, a plurality of the following features, namely, leaves of semi-glossy and rather leathery texture of medium to large size; peduncles which are almost entirely smooth; notably large flowers, containing in the neighborhood of 45 to 50 petals, and ranging from deep pink to light red in color, said flowers having a moderate to strong damask fragrance, and giving place to medium-sized hips of globular formation and generally russeted surface, at maturity.

No references cited.

ROBERT E. BAGWILL, Primary Examiner